(12) United States Patent
Herrenbauer et al.

(10) Patent No.: US 8,888,755 B2
(45) Date of Patent: Nov. 18, 2014

(54) DISPOSABLE BAG COMPRISING A MULTILAYER FILM

(75) Inventors: Michael Herrenbauer, Neu-Anspach (DE); Manfred Weis, St. Wendel (DE); Franz Kugelmann, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 38 days.

(21) Appl. No.: 13/130,176

(22) PCT Filed: Nov. 19, 2009

(86) PCT No.: PCT/EP2009/008248
§ 371 (c)(1),
(2), (4) Date: Jun. 23, 2011

(87) PCT Pub. No.: WO2010/057643
PCT Pub. Date: May 27, 2010

(65) Prior Publication Data
US 2011/0249916 A1    Oct. 13, 2011

(30) Foreign Application Priority Data
Nov. 20, 2008    (DE) .................. 10 2008 058 272

(51) Int. Cl.
*A61B 19/00*    (2006.01)
*A61M 1/16*    (2006.01)
(52) U.S. Cl.
CPC ........... *A61M 1/1656* (2013.01); *A61M 1/1668* (2013.01)
USPC ............................ 604/408; 604/403; 604/410
(58) Field of Classification Search
CPC ......... A61J 1/10; A61J 1/1475; A61J 1/1406; A61J 1/2093; A61J 2001/201; A61J 2001/2024; B29L 2031/7148; A61M 1/0209; A61M 1/1656; A61M 2001/1688; B32B 27/08; B32B 27/32; C08L 23/0815; C08J 5/18
USPC .................................. 604/403–410; 428/35.2
See application file for complete search history.

(56) References Cited

U.S. PATENT DOCUMENTS

| | | | |
|---|---|---|---|
| 4,326,526 A * | 4/1982 | Buck et al. ..................... | 604/29 |
| 4,396,382 A | 8/1983 | Goldhaber | |
| 4,767,526 A | 8/1988 | Vantard | |
| 4,778,697 A * | 10/1988 | Genske et al. ............... | 428/35.2 |

(Continued)

FOREIGN PATENT DOCUMENTS

| DE | 26 49 657 A1 | 5/1978 |
|---|---|---|
| DE | 197 28 686 C1 | 4/1999 |

(Continued)

OTHER PUBLICATIONS

International Search Report of PCT/EP2009/008248 (Jan. 5, 2010).

(Continued)

*Primary Examiner* — Philip R Wiest
*Assistant Examiner* — Ariana Zimbouski
(74) *Attorney, Agent, or Firm* — Millen, White, Zelano & Branigan, P.C.

(57) ABSTRACT

The present invention relates to a disposable bag which comprises a multilayer film for accommodating a fluid, and a device which comprises a support holder for the disposable bag according to the invention in which the disposable bag is arranged. The present invention also relates to a process for the production of the disposable bag.

20 Claims, 6 Drawing Sheets

(56) References Cited

U.S. PATENT DOCUMENTS

| | | | |
|---|---|---|---|
| 4,994,021 A * | 2/1991 | Smith et al. | 604/6.04 |
| 6,017,598 A | 1/2000 | Kreischer et al. | |
| 6,468,259 B1 * | 10/2002 | Loretti et al. | 604/410 |
| 7,569,262 B2 | 8/2009 | Szabo et al. | |
| 2003/0135193 A1 | 7/2003 | Hilgers et al. | |
| 2004/0078023 A1 * | 4/2004 | Gollier et al. | 604/410 |
| 2004/0146671 A1 | 7/2004 | Szabo et al. | |
| 2005/0238830 A1 * | 10/2005 | Karsten et al. | 428/35.2 |
| 2006/0246244 A1 * | 11/2006 | Jenkins et al. | 428/35.2 |
| 2008/0176016 A1 * | 7/2008 | Tateishi et al. | 428/35.7 |
| 2010/0280485 A1 * | 11/2010 | Choi et al. | 604/410 |

FOREIGN PATENT DOCUMENTS

| | | |
|---|---|---|
| DE | 198 25 158 C1 | 4/1999 |
| DE | 199 59 230 C1 | 4/2001 |
| ES | 2203638 T3 | 3/1996 |
| JP | 2004-526819 | 9/2004 |
| WO | WO 83/02061 A1 | 6/1983 |

OTHER PUBLICATIONS

German PTO Office Action in DE102008058272.2 issued Dec. 12, 2012 and partial English Translation of same.

* cited by examiner

DISPOSABLE BAG COMPRISING A MULTILAYER FILM

The present invention relates to a disposable bag for accommodating a fluid, which comprises a multilayer film, and a device which comprises a support holder for the disposable bag according to the invention, in which the disposable bag is arranged. The present invention also relates to a process for the production of the disposable bag.

Various versions of haemodialysis equipment are known. The exchange of substances between the blood and the dialysis fluid takes place in a dialyzer which has a first flow path for the blood and a second flow path for the dialysis fluid, wherein both flow paths are separated from each other by a semipermeable membrane. The first flow path is part of an extracorporeal blood circulation system with a feed line and a return line for the blood and also optionally a pump supporting the blood flow. The second flow path is connected to equipment feeding and removing the dialysis fluid.

Containers of the haemodialysis machines known from the state of the art often consist of glass which, because of the pore-free surface, are superior, as regards hygiene and bacteriology, to other materials. In addition, glass is largely resistant to chemicals coming into consideration, can be satisfactorily cleaned and is physiologically harmless.

Known haemodialysis equipment is characterized by a relatively simple structure. However, a disadvantage is that the glass container is relatively expensive to produce. Furthermore, the disinfection of the glass container that is required before the dialysis treatment proves disadvantageous, as a rapid re-use of the container is often necessary. It would therefore be desirable to provide a haemodialysis apparatus in which the apparatus can continue to be used during the required disinfection of the container which contains the dialysis fluids.

To achieve this object U.S. Pat. No. 4,767,526 proposes a dialysis machine in which a reservoir in which the dialysis fluid is held is lined with a bag which is discarded after use. This has the advantage that the reservoir is quickly available again after the removal of the bag and the reservoir itself need not be disinfected.

DE 198 25 158 C1 describes a large-capacity bag which is welded together from two conical film sheets. In order to ensure a more certain separation of fresh dialysis fluid and used dialysate, an additional separating film can be welded into the bag.

EP 1 235 601 B1 describes a bag for holding dialysate in a tank. To introduce this bag into the container, a special folding mechanism is used from which the bag is unfolded from a handy format to form the bag.

WO 83/02061 describes a bag made of PVC (polyvinylchloride) with several chambers for peritoneal dialysis. This bag is used for the separate storage of components of the dialysis solution which are removed separately and are to be mixed only when they are administered to the patient. A disadvantage of this bag is that it consists of PVC.

Although the use of the abovementioned bag in dialysis machines solves the problem that the tank itself no longer needs a time-consuming disinfection, these bags are disadvantageous as regards their size and the concomitant awkward handling.

These relatively large-surface bags can lead to problems during everyday activities in the clinic, as a bag usually has to be changed rapidly by sometimes poorly trained clinic staff. Thus the large surface of the bag harbours the danger of incorrect use when the bag is introduced into the inside of the tank. The bag can thereby be wrongly crumpled with the result that it does not unfold fully when filled with the dialysate.

In addition, residual quantities may prove non-removable when removing fluid due to creasing. Dialysis bags have inlets and outlets in order to be able to drain or feed fresh or used dialysate. In addition, if the bag is incorrectly folded or crumpled because it has been introduced into the reservoir too quickly, creases can form in the bag such that the essential openings are partly or wholly closed.

Attempts to already introduce specially (pre)folded disposable bags into the device, intended to prevent an incorrect unfolding, were likewise not successful. In addition, to date no folding of large-surface disposable bags has been ascertained which fully prevented unfolding problems.

A further problem with the disposable bags of the state of the art is their deficient stability, in particular when they have to accommodate large volumes such as are important in particular for the present invention. This is attributable in particular to the fact that the weight or the pressure which bears on the weld seams increases markedly as the fill quantity increases. A further disadvantage of the known bags is that, because of their size, a large quantity of material needs to be used, which in turn brings with it a large volume of waste.

The object of the invention was therefore to provide a disposable bag or a device which is suitable for filling with dialysis fluid which does not require the time-consuming disinfection of the reservoir of the dialysis machine, makes possible a secure, rapid and creasing-free handling when introducing the disposable bag into the reservoir of the dialysis machine in everyday activity in the clinic, requires less material and brings with it a high stability of the bag, i.e. high transport security when inserting and removing the filled disposable bag/device into/from the reservoir.

The object is achieved according to the invention by a disposable bag comprising a multilayer film for accommodating a fluid, wherein the multilayer film has a tensile elongation in longitudinal direction of the extrusion of the film of 250% to 850%, preferably 400% to 800%, more preferably 500% to 750% and most preferably 600% to 700%, and in transverse direction of the extrusion of the film of 300% to 1050%, preferably 450% to 1000%, more preferably 600% to 900% and most preferably 700% to 800%.

By tensile elongation or elongation at break is meant the percentage ratio of the change in length $\Delta L$ (at break) to the starting length. It expresses the capacity of a material to follow changes in shape without cracking. Tensile elongation is measured in the tensile test according to DIN 53455.

A great capacity of the film to change its length in longitudinal direction of the extrusion of the film in the abovementioned range has the advantage according to the invention that, while it is being filled with or emptied of (used or fresh) dialysate, the bag experiences a change in volume without forming cracks before the given upper limits. This brings with it the further advantage that when unfilled only a small amount of material is required, but there is nevertheless a large capacity when filled. A product can thereby be provided which brings with it only a small amount of waste. This is particularly advantageous from environmental points of view.

By "disposable bag" is meant any item which makes it possible to accommodate a fluid, a solid and/or a gas for a specific period. In addition by a disposable bag is meant within the framework of the present invention any item which is suitable for use at least once in the intended application.

By "multilayer film" is meant in the present invention a film which consists of two or more layers of different or the same material which are joined together by adhesion.

It is preferred within the framework of the present invention that the multilayer film is built up from 2 to 10 layers, wherein a structure of 2 to 5 layers is more preferred and a structure of 3 or 4 layers is particularly preferred. The multilayer film can be produced according to any process which is known to a person skilled in the art as suitable for the purpose according to the invention.

In a further embodiment of the present invention, it is preferred that the multilayer film of the disposable bag according to the invention has a tear strength in longitudinal direction of the extrusion of the film of 300 N/mm² to 350 N/mm², preferably 310 N/mm² to 340 N/mm² and more preferably 320 N/mm² to 330 N/mm², and in transverse direction of the extrusion of the film of 220 N/mm² to 270 N/mm², preferably 230 N/mm² to 260 N/mm² and more preferably 240 N/mm² to 250 N/mm².

By "tear strength" is meant tensile stress which is exerted on an item at the moment of tearing. The tear strength is measured in the tensile test according to DIN 53455. A tear strength below the abovenamed lower limit is disadvantageous, as the bag otherwise tears prematurely through overextension. Although the bag is very tear-resistant above the cited upper limit, it is not sufficiently extensible.

In a further embodiment of the present invention the multilayer film of the disposable bag according to the invention preferably has a transverse strain ratio μ in the rubber-elastic state of 0.45 to 0.55, more preferably 0.47 to 0.53 and most preferably 0.49 to 0.51.

The transverse strain ratio, also called Poisson's ratio, is defined as the ratio of relative change in thickness Δd/d to the relative change in length Δl/l upon exposure to an external force or stress.

A further embodiment according to the invention is a disposable bag in which the multilayer film can be extended by up to 500% by a force of preferably 45 N to 60 N, more preferably 48 N to 62 N, most preferably 52 N to 58 N. To measure the extensibility a weight which corresponds to a specific force in N is applied uniformly to a 15-mm wide film and the change in length measured.

A high extensibility has the advantage that the bag is small when unfilled and thus easy to handle. In addition, the material requirement is small as a result of the marked extensibility of the material. A simpler manufacture and packaging of the material is thus also made possible.

A particularly preferred embodiment of the present invention is also a disposable bag in which the ratio of the external surface of the disposable bag when filled to the maximum to the external surface when unfilled is in the region of preferably 5/1, greater than ≥2/1, more preferably ≥5/1.

Typical upper limits are approx. 8/1 to 12/1 e.g. 10/1 or 9/1. However, higher ratios are provided according to the invention.

By "external surface" is meant the surface of the bag which can come into contact with its surroundings (air) when filled and also unfilled. The term "when filled to the maximum" is described by the maximum size of the bag at which the bag still just forms no cracks and consequently does not yet tear.

By "when unfilled" is meant the state of the bag in which the inside of the bag is essentially not filled by material of any kind, i.e. essentially occupies no space.

The property of the increase in surface depending on the quantity filled ensures that the multilayer film of the bag is always under pressure during filling, with the result that as it increasingly filled this pressure increases and any folds in the multilayer film which are present when unfilled increasingly disappear. This has the advantage according to the invention that a crease-free introduction of the disposable bag into a reservoir of a medical apparatus, in particular dialysis machine, is ensured. Thus the complete removal of the fluid from the bag is also ensured.

A further embodiment of the present invention is also a disposable bag in which the ratio of the capacity of the disposable bag when filled to the maximum to the capacity in the state in which the multilayer film is unextended is preferably ≥3/1, for preference ≥5/1. Typical non-limiting ranges are 3/1 to 12/1, more preferably 5/1 to 11/1, still more preferably 7/1 to 10/1 and most preferably 8/1 to 9/1.

However, other higher upper limits are also possible according to the invention.

By "capacity in the state in which the multilayer film is unextended" is meant the volume which can be poured into the bag without an extension of the multilayer film.

In a further embodiment of the present invention the disposable bag of the abovenamed embodiments preferably has a capacity in when filled to the maximum in the range of 30 L to 120 L, particularly preferably 40 L to 110 L, still more preferably 50 L to 100 L, further preferably 60 L to 90 L and most preferably 70 L to 80 L.

The disposable bag of the present invention can contain one chamber or more than one (several) chambers. By "several" is meant the presence of at least 2 chambers. However, the disposable bag can have as many chambers as appears suitable to a person skilled in the art for the respective intended use.

The disposable bag preferably contains 1 to 10 chambers, preferably 2 to 6 chambers, more preferably 2 to 4 and most preferably 2 or 3 chambers.

If the disposable bag contains only one chamber, two disposable bags can also be used in the dialysis machine, one for the preparation of fresh dialysate and one into which used dialysate is recycled. However, if the disposable bag contains several chambers, preferably one of the chambers is used for the preparation of fresh dialysate, and one chamber for collecting used dialysate.

Such a use of the bag(s) according to the invention has the advantage that a separation of fresh and used contents is possible and thus no cross-contamination occurs. In addition, there is no need to drain water at the place of use, because as a result of using one bag with several chambers or two or more bags with one chamber the used dialysate can be collected in one chamber. The individual chambers are preferably likewise manufactured from parts of the multilayer film as defined in more detail below.

Within the framework of the present invention a preferred embodiment of the disposable bag is equipped with chambers which are arranged in longitudinal direction of the disposable bag.

The individual chambers can each have one or more feed and drainage line(s), wherein it is preferred that—particularly in the case of a disposable bag with 2 chambers—at least one chamber has a feed line and the other chamber has a drainage line. However, each individual chamber can also have a feed and drainage line.

The feed and drainage line(s) can be welded fast to the disposable bag or else be fixedly or removably connected via a sealing system. The hose connections to the disposable bag can be conventional connectors. Decisive is that the disposable bag can be rapidly attached to the feed and drainage line(s) or removed again to replace the disposable bag. However, it is also possible that the feed and drainage line system is formed in one piece with the disposable bag.

In a further embodiment according to the invention, the multilayer film of a disposable bag comprises a type (A) layer which contains several components, wherein one of the components is selected from the group which consists of styrene-isoprene block copolymers, styrene-ethylene-butylene-styrene block copolymers, styrene-ethylene-butylene block copolymers, styrene-ethylene-propylene block copolymers and mixtures thereof, and a further component is selected from the group which consists of polyethylene and a statistical copolymer which comprises ethylene units.

The further component in the type (A) layer is particularly preferably a statistical copolymer which consists of ethylene and octene units.

The proportion of one component in the type (A) layer can be in the range of 35% to 99.99%, preferably 50% to 99.9%, more preferably 55% to 99%, still more preferably 60% to 95% and most preferably 60% to 90%, relative to the total composition of the type (A) layer.

The further component in the type (A) layer can thus be in the range of 0.01% to 65%, preferably 0.1% to 50%, more preferably 1% to 45%, still more preferably 5 to 40% and most preferably 10% to 40%, relative to the total composition of the type (A) layer.

The multilayer film also preferably comprises one or more type (B) layers which contains several components independently of one another, wherein one of the components is selected from the group which consists of styrene-ethylene-butylene block copolymers (SEBs), styrene-ethylene-butylene-styrene block copolymers (SEBSs), styrene-ethylene-propylene block copolymers (SEPs), styrene-isoprene-styrene block copolymers (SISs) and mixtures thereof, and a further component is selected from the group which consists of polypropylene and a statistical copolymer which comprises propylene units.

It is particularly preferred that the further component in the type (B) layer consists of a statistical copolymer which comprises propylene and ethylene units.

Films with a type (B) layer are advantageous in respect of their high extensibility. The proportion of one component in the type (B) can be in the range of 35% to 99.99%, preferably 50% to 99.9%, more preferably 55% to 99%, still more preferably 60% to 95% and most preferably 60% to 90%, relative to the total composition of the type (A) layer.

The further component in the type (B) layer can thus lie in the range of 0.01% to 65%, preferably 0.1% to 50%, more preferably 1% to 45%, still more preferably 5 to 40% and most preferably 10% to 40%, relative to the total composition of the type (B) layer.

In a quite particularly preferred embodiment of the present invention the multilayer film is preferably built up from a laminate of 3 layers. The middle layer is preferably a layer of the abovenamed type (A). The two external layers which surround the type (A) layer are preferably type (B) layers.

These type (B) external layers can have an identical composition or different composition(s) from one another.

These films are particularly preferred, as they ensure a uniform extension of the disposable bag according to the invention throughout the filling.

By "polyethylene" is meant within the framework of the present invention a thermoplastic produced by the polymerization of ethylene with the simplified chain-structure formula $(C_2H_2)_n$. A copolymer which comprises ethylene units is a polymer produced by copolymerization of ethylene with any chosen further olefin. Polyethylene and a copolymer which comprises ethylene units belong to the group of the polyolefins.

The so-called "further olefin" is preferably an α-olefin which comprises 3 to 20 carbon atoms. Examples of any chosen further olefin are propylene, butene, pentene, hexene, heptene and octene, wherein octene is particularly preferred.

By "polypropylene" is meant within the framework of the present invention a thermoplastic produced by polymerization of propylene with the simplified chain-structure formula $(C_3H_6)_n$. A copolymer which comprises propylene units is a polymer produced by copolymerization of propylene with any chosen further olefin. Polypropylene and a copolymer which comprises propylene units belong to the group of the polyolefins.

The so-called "further olefin" is preferably an α-olefin which comprises 2 to 4 carbon atoms. Examples of any further chosen olefin are ethylene, butene, pentene, hexene, heptene and octene, wherein ethylene is particularly preferred.

Known trade names of various polyolefins are: Alathon®, Dyneema®, Hostalen®, Lupolen®, Polythen®, Spectra®, Trolen®, Vestolen®.

A distinction is generally drawn between:

PE-HD (HDPE): weakly-branched polymer chains, therefore high density between 0.94 g/cm³ and 0.97 g/cm³, ("HD" stands for "high density").

PE-LD (LDPE): strongly-branched polymer chains, therefore low density between 0.915 g/cm³ and 0.935 g/cm³, ("LD" stands for "low density").

PE-LLD (LLDPE): linear low-density polyethylene, the polymer molecule of which has only short branches. These branches are produced by copolymerization of ethene and higher α-olefins (typically butene, hexene or octene) ("LLD" stands for "linear low density").

PE-HMW: high-molecular-weight polyethylene. The polymer chains are longer than in the case of PE-HD, PE-LD or PE-LLD, the average molecular mass is 500 kg/mol to 1000 kg/mol.

PE-UHMW: ultra-high-molecular-weight polyethylene with an average molecular mass of up to 6000 kg/mol and a density of 0.93 g/cm³ to 0.94 g/cm³ ("UHMW" stands for "ultra high molecular weight").

The above-named copolymers which comprise at least ethylene and propylene units are preferably statistical copolymers. A statistical copolymer is a copolymer in which the at least two different monomer units from which the polymer is composed are present copolymerized in a random sequence. By the above-named block copolymers is meant polymers in which the monomers are not statistically incorporated into the chain but in homopolymeric chain sections which are joined to one another.

They represent a mid-point between a copolymerizate and a polymer mixture and offer the possibility of improving polymers without changing the monomer composition.

Preferred examples of such block polymers include the following: mixed block copolymers of ethylene, propylene, alpha olefins or isoprene and styrene (so-called olefinic styrene block copolymers) or diene-styrene block copolymers such as e.g. SEBS, SEPS, SBS, SEB, SEP and SIS etc.

Preferred alternatives to be used in the layer of types (A) and (B) are also elastomeric styrene-butadiene or styrene-isoprene block copolymers, preferably with a diene proportion of over 50 wt.-%, but also for example resinous styrene-butadiene and styrene-isoprene block copolymers, preferably with a diene content of under 50 wt.-%, relative to the total weight of the copolymer.

If elastomeric styrene-diene block copolymers with a diene content of over 50 wt.-% are used, then their proportion in the mixture is preferably between 20 wt.-% and 40 wt.-% but can also be higher or lower, as required. Resinous styrene-diene block copolymers containing over 50 wt.-% styrene, in particular those with, say, 65 wt.-% to 95 wt.-% styrene, are preferably to be contained in a quantity of 40 wt.-% to 60 wt.-

% in the moulding compound according to the invention. In a further embodiment it is preferred that the disposable film is free from polyvinylchloride.

In an extremely preferred embodiment of the present invention the multilayer film is built up from 3 layers, wherein the first external layer contains 60 wt.-% styrene-ethylene-butylene-styrene (SEBS) copolymer and 40 wt.-% statistical polypropylene-ethylene copolymer, the middle layer 60 wt.-% styrene-ethylene-butylene-styrene block copolymer and 40 wt.-% statistical polyethylene-octene copolymer and the second external layer 60 wt.-% styrene-ethylene-butylene-styrene block copolymer (SEBS) and 40 wt.-% statistical polypropylene-ethylene copolymer.

It is further preferred within the framework of the present invention that the multilayer film can be heat-sterilized. It is possible that only one layer of the multilayer film can be heat-sterilized, but two or more or even all the layers of the multilayer film can also be heat-sterilized. It is particularly preferred that at least the layer which forms the inside of the disposable bag according to the invention can be heat-sterilized.

By "heat-sterilizability" is meant here that the multilayer film retains both its outer shape and also its mechanical and physico-chemical properties during and after the treatment with steam at a temperature in the range of 100 to 140° C., preferably 110 to 130° C. and a pressure of 1 to 2 bar.

The thickness of the multilayer film preferably lies in a range of 1 µm to 1000 µm, more preferably from 5 µm to 800 µm, particularly preferably from 8 µm to 500 µm and most preferably from 10 µm to 150 µm. It is possible that the individual layers of the multilayer film each have the same thickness or different thicknesses. It is particularly preferred, in the case of a 3- or more-layered multilayer film, that the two layers forming the outsides have a thickness of ≤40 µm, preferably ≤20 µm.

The inner layer of a 3- or more-layer film can preferably have a thickness of ≥500 µm, more preferably of ≥300 µm and most preferably of ≥100 µm, whereby a good stability and elasticity is achieved. A high flexibility and load-change resistance is thereby achieved.

According to a preferred version of the present invention at least one layer of the multilayer film also has additives and impurities, such as e.g. catalyst residues, at a level under 5000 ppm and under 200 ppm.

It is further preferred that in the case of a 3- or more-layer film the respective external layers are formed by heat-sterilizable layers. The resultant advantage is that, during the heat sterilization, neither the insides of the disposable bag nor the outsides of the disposable bag can stick to other components.

It is further preferred that at least one layer of the multilayer film can be sealed, preferably heat-sealed. The sealing temperature preferably lies in the range of 160° C. to 230° C., more preferably in the range of 180° C. to 210° C.

It is also preferred that the multilayer film is biocompatible and particularly preferably haemocompatible.

It is furthermore preferred that the multilayer film is a transparent film.

The multilayer film is furthermore preferably free from lubricants, plasticizers, antiblocking agents, antistatics and fillers.

The present invention also relates to a device which comprises a support apparatus in which a disposable bag according to the invention is arranged. The support apparatus is preferably such that it supports/stabilizes the disposable bag at those points at which welding points threaten to tear first. The object is thus achieved to remove the disposable bag quickly and safely from the reservoir and to absorb the pressure at the weak points of the bag after it has been filled. In this way it is thus possible to introduce and remove an elastic container without the above-named problems, such as creasing, competently and quickly into and from a reservoir.

The support apparatus for accommodating the disposable bag according to the invention preferably comprises a holder which is preferably such that the disposable bag can be attached thereto when filled and also unfilled. Furthermore, the support apparatus must be large enough to be able to also hold the disposable bag in an expanded volume corresponding to the application, i.e. have at least the above-named maximum holding capacity of the disposable bag. Preferably the support apparatus has a receiving unit formed as a shaping dish. The shaping dish has a central cylindrical bearing surface to which are connected an outwardly curved upper bearing surface and an outwardly curved lower bearing surface.

The shapes of the preferably vessel-like support apparatus are not subject to any limitations. Wholly differently curved and differently shaped insides of the support apparatus can be used if this is required for technical or aesthetic reasons. A secure storage of the dialysate is guaranteed by the elastic bag in every case.

The advantage of such a shaping dish is that the pressure of a filled disposable bag possibly found therein is well absorbed. In other words, for a medical treatment such as haemodialysis or peritoneal dialysis, the disposable bag is placed in the shaping dish preferably present in the support apparatus.

When it is being filled with ready-to-use dialysate the bag according to the invention rests against the wall of the shaped support apparatus and is securely surrounded and supported by same. This security is not guaranteed with previous "batch dialysis" bags. As the dialysate is introduced first into the bag and the support apparatus generally contains bicarbonate as a component, a gas pressure is exerted on the bag wall by the gaseous $CO_2$ in equilibrium with dissolved bicarbonate. $CO_2$ could escape through the film material and the composition of the dialysate would not be constant. This is effectively prevented by the elastic bag wall resting against the dish of the support apparatus. The support apparatus thus additionally acts as the gas barrier in the systematic arrangement comprising the bag and support apparatus according to the invention.

In a further preferred embodiment, the disposable bag according to the invention is provided at the top and/or bottom end with a holder, preferably in the form of a securing strip, via which it can be secured to the apparatus.

With the help of the holder the disposable bag can thus be introduced into the apparatus and also removed again. It is particularly preferred that the feed and/or drainage line also be secured via the holder.

The holder can be either connected securely to the disposable bag or releasably attached. In the first case the holder is also an item which discarded together with the disposable bag according to the invention.

Within the meaning of the present invention it is also possible that more than one of the disposable bags according to the invention is attached in a holder or else several of the disposable bags according to the invention can each be attached to a holder in an apparatus.

The present invention also relates to the use of the disposable bag according to the invention or the device according to the invention for use in an apparatus in for carrying out medical treatment.

In a further embodiment of the present invention the apparatus named in the last section is an apparatus for carrying out haemodialysis or peritoneal dialysis, i.e. the medical treatment is haemodialysis or peritoneal dialysis.

The present invention also relates to a process for the production of the disposable bottle according to the invention. The process comprises the following steps:
a) production of a multilayer film as defined above; and
b) welding the multilayer film into a disposable bag.

In a preferred embodiment the process according to the invention also comprises the step of dividing the multilayer film into several parts. This step is preferably carried out before step b) of the above-defined process.

The process according to the invention for the production of a multilayer film according to the invention is characterized in that the multilayer film is preferably produced by coextrusion. To produce the multilayer film according to the invention the starting materials are mixed, compounded and granulated, before being coextruded preferably on a water-cooled blown-film line.

It is preferred that the layers of the multilayer film are coextruded in direct contact with one another. It is also within the framework of the present invention that a protective film produced by coextrusion is attached on one or both sides of the multilayer film. This/these protective film/s can be easily removed or pulled off the multilayer film according to the invention without leaving a residue.

Furthermore, the multilayer film can however also be produced in a separate extrusion process, a calendering process or in a film-casting process. The co-extrusion structure can be smoothed immediately after extrusion to produce a smooth surface. If a smoothing is desired, the multilayer film can however also be smoothed by any other process known as suitable to a person skilled in the art.

The invention is described in more detail using the following preferred embodiments in conjunction with the Figures, with the sole aim of explaining and illustrating the invention while neither limiting nor restricting the scope of the invention.

There are shown in:

FIG. 1 a disposable bag according to the invention with 2 chambers, each with a feed and a drainage line FIG. 2 a disposable bag according to the invention with a holder in the form of a securing strip.

FIG. 3 a disposable bag according to the invention with 2 holders in the form of securing strips.

FIG. 4 a force [N]/extension [%] diagram of the multilayer film of the disposable bag according to the invention FIG. 5 a force [N]/extension [%] diagram of comparison film 1.

FIG. 6 a force [N]/extension [%] diagram of comparison film 2.

FIG. 1 shows a disposable bag according to the invention (1). The disposable bag according to the invention (1) is shown in side view. The disposable bag is divided by a dividing wall/dividing film (4) into 2 chambers, each of which is provided with a feed or drainage line ((2), (3)).

Figure 1:
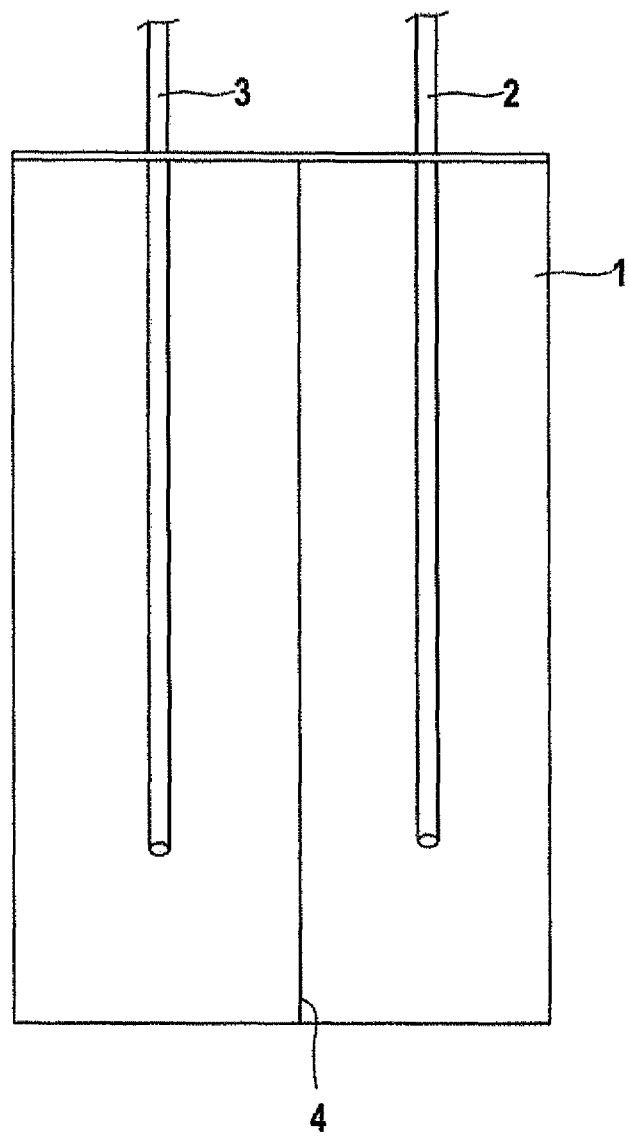
Figure 2:
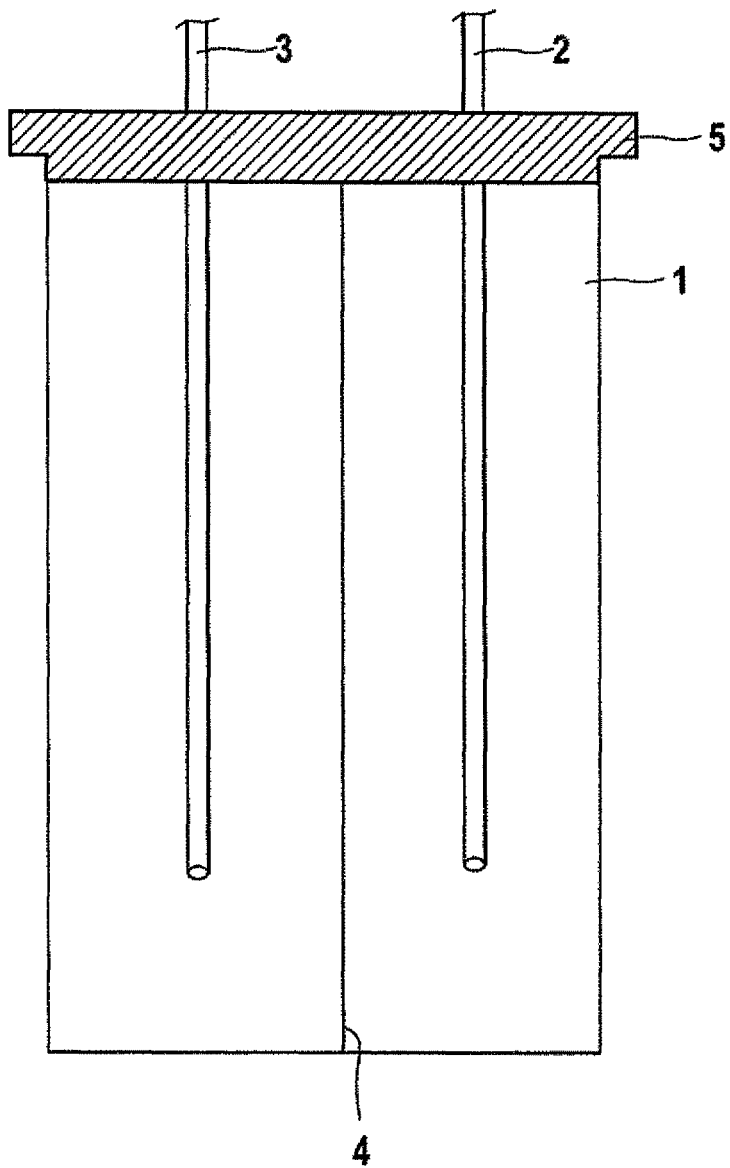
FIG. 2 shows the disposable bag according to the invention of FIG. 1, which is also equipped at the top, to which the feed and drainage line ((2), (3)) are also attached, with a holder (5) in the form of a holding bar. The holding bar (5) can also serve to fix the feed and drainage lines ((2), (3)).
Figure 3:
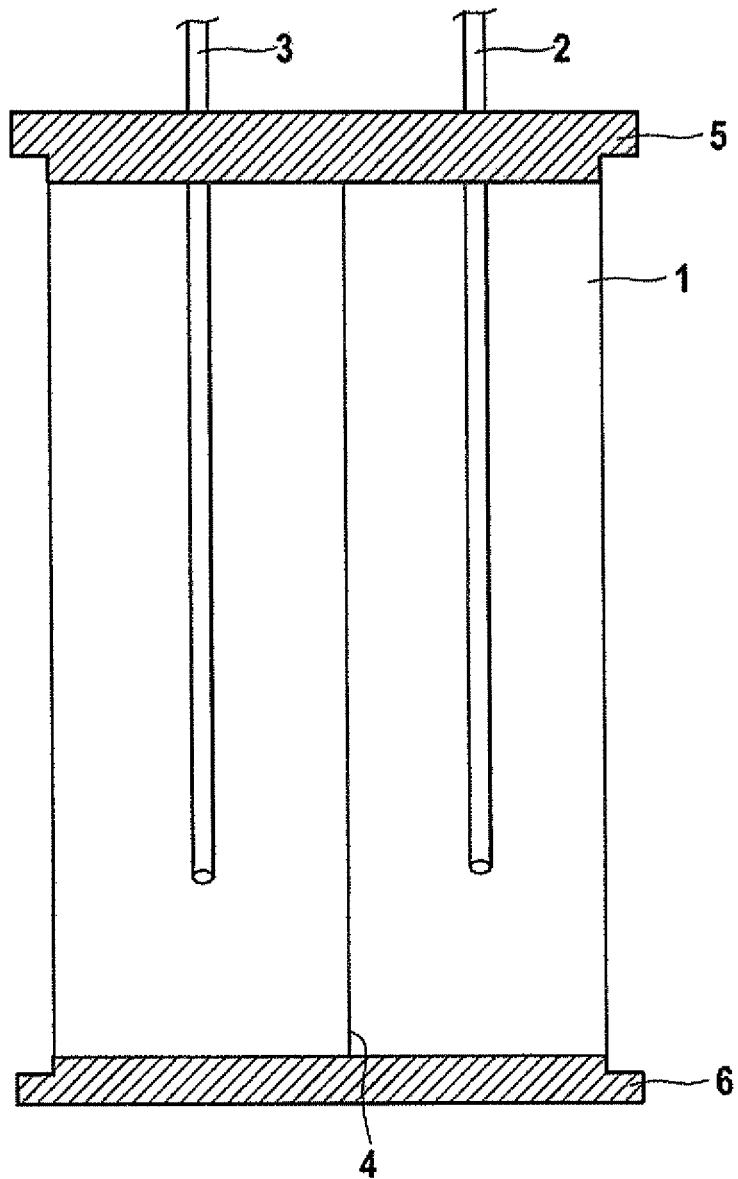
FIG. 3 shows the disposable bag according to the invention from FIG. 2, which is also equipped at the bottom with a holder (6) in the form of a holding bar.
Figure 4:
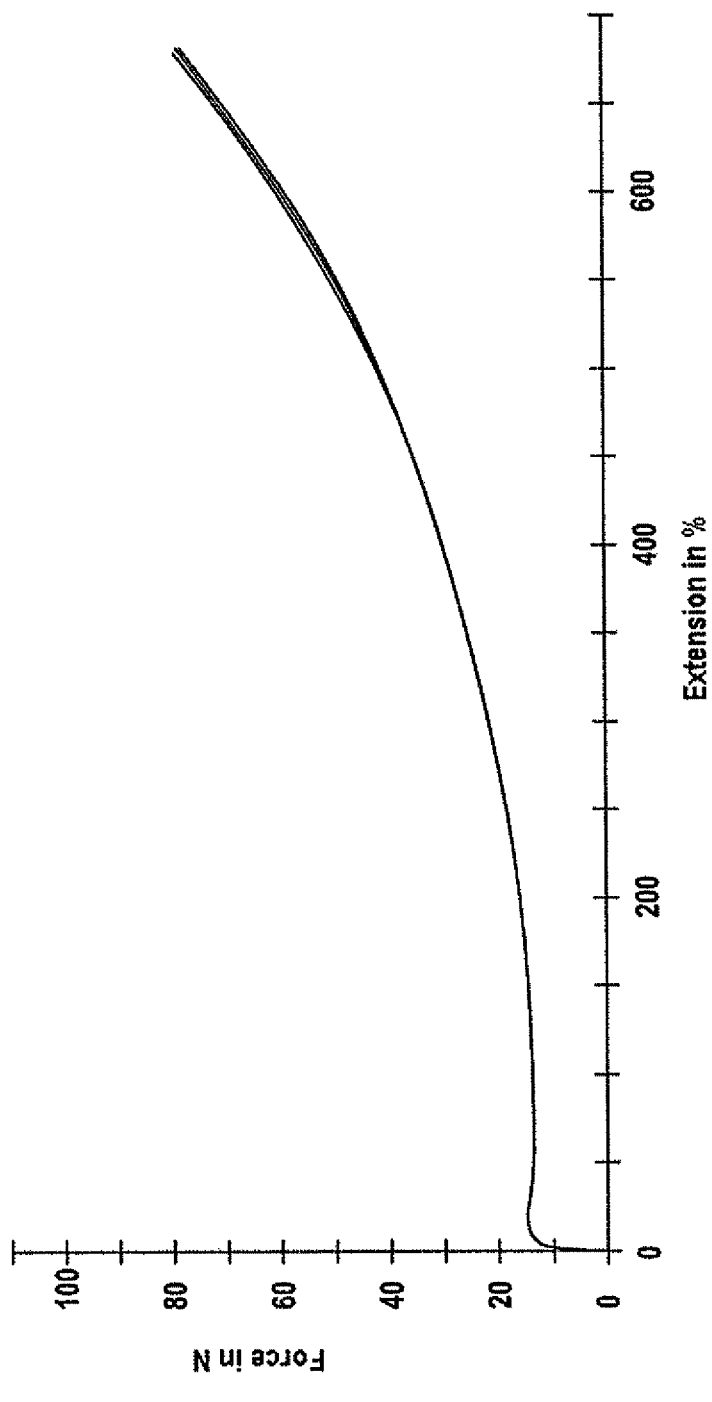
FIG. 4 shows a force [N]/extension [%] diagram of the multilayer film of a disposable bag according to the invention.
Figure 5:
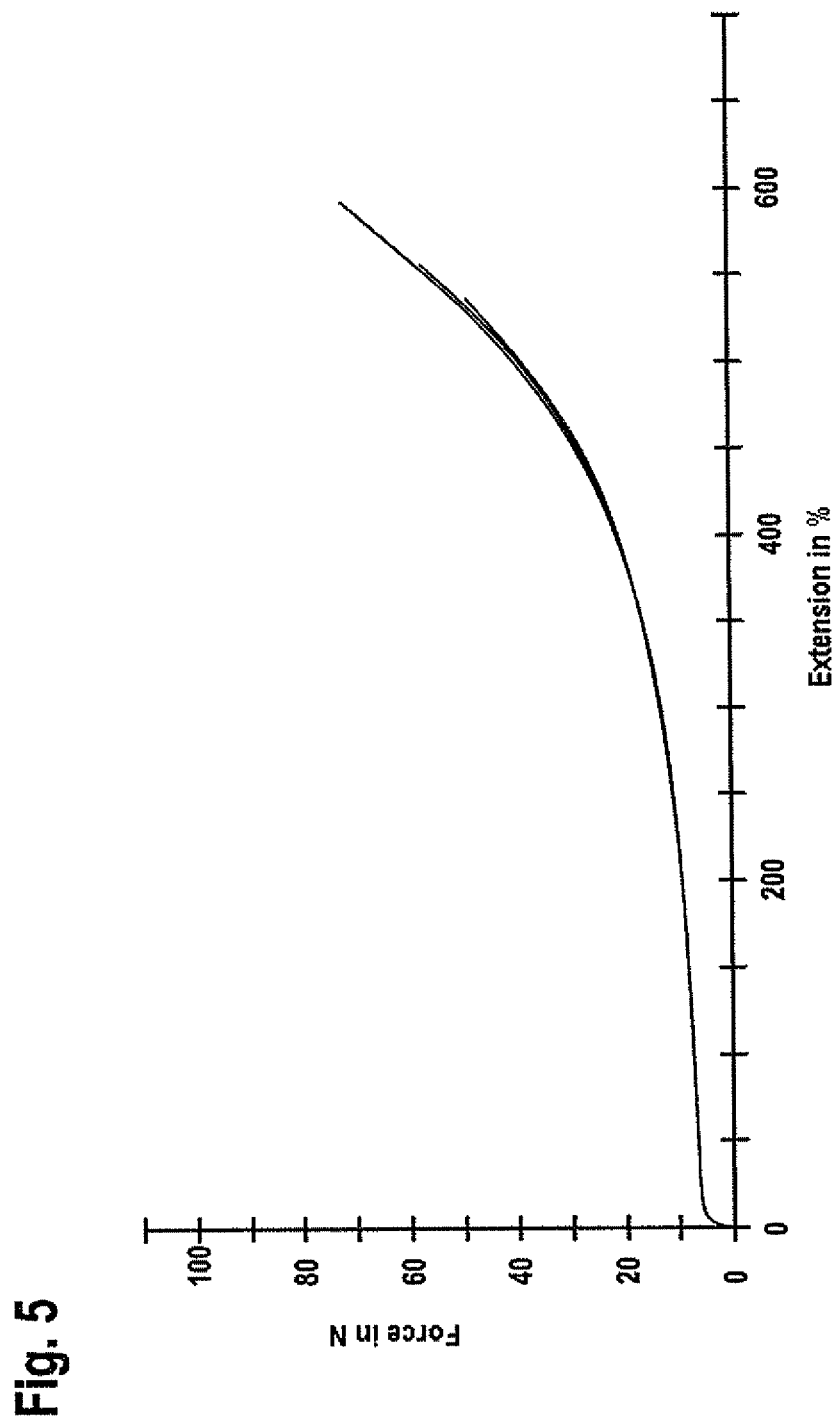
Figure 6:
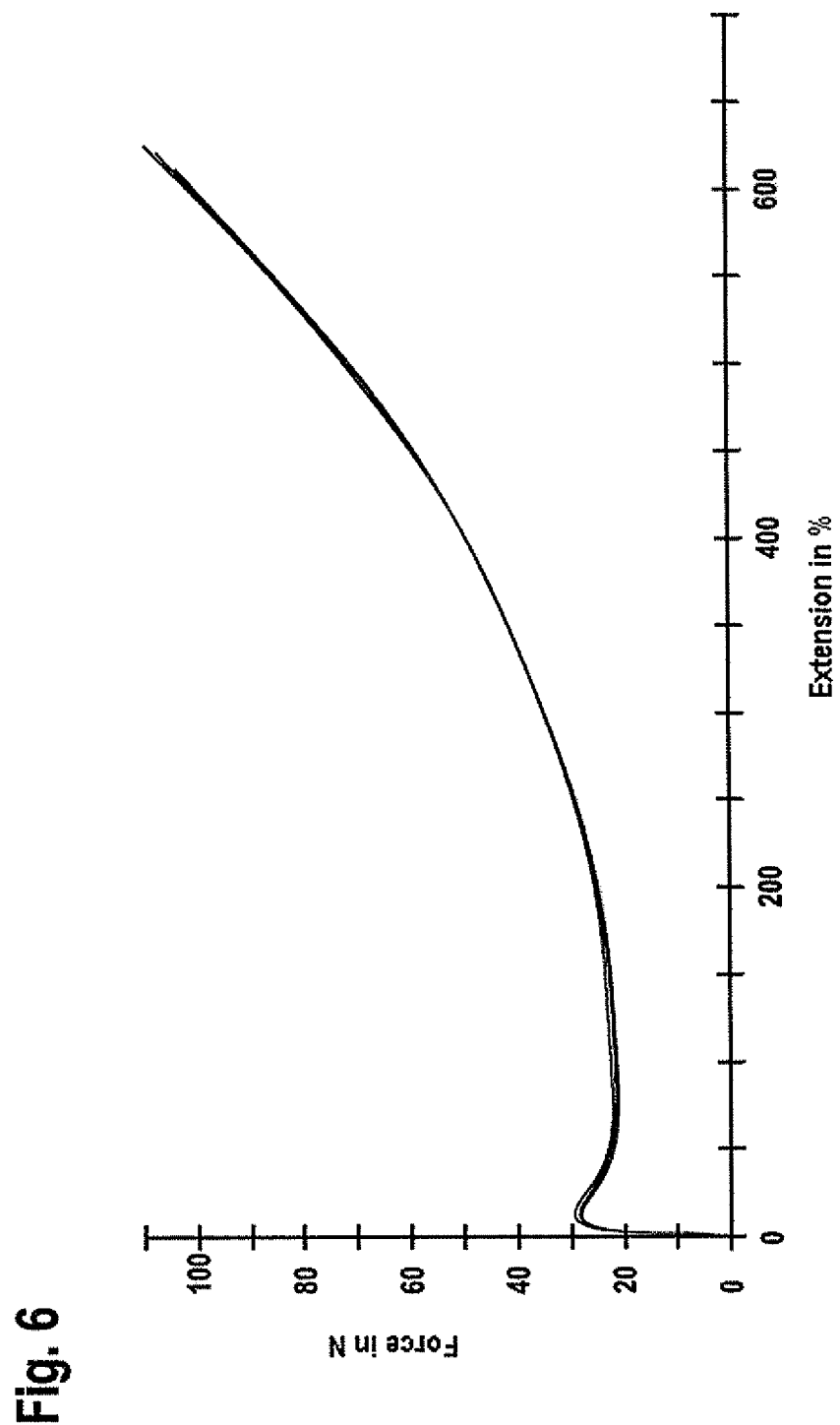

In FIGS. 5 and 6 a force [N]/extension [%] diagram of comparison films 1 (FIGS. 5) and 2 (FIG. 6) is shown.

EXAMPLES

In the following examples the advantages of the multilayer film used for the disposable bag according to the invention are illustrated. It is pointed out that the examples and the compositions named in the examples of the multilayer film are purely illustrative and in no way limit the scope of the invention.

The specimens 1-3 named in the embodiment examples 1 to 5 have the following structure:

Specimen 1

Specimen 1 is a three-layer film with the following structure:
Compound A: 10 μm
Compound B: 130 μm
Compound A; 10 μm
The external layers, and also the characteristic layer of the multilayer film according to specimen 1, contains a styrene-ethylene-propylene (SEP) block copolymer.
The composition of specimen 1 is as follows:
Compound A: 100 parts SEP (Septon 2005; Kuraray) 70 parts PP-R Co (PP 23M 10cs264; Rexene)
Compound B: 100 parts SEP (Septon 2005; Kuraray) 100 parts PE copolymer (Engage; DOW) (ρ<0.9 g/cm$^3$) 70 parts PP-R Co (PP 23M 10cs264; Rexene)
The abbreviations mean:
SEP: Styrene-ethylene-propylene block copolymer
PP-R Co: Polypropylene random copolymer
PP: Polypropylene
PE: Polyethylene.

Specimen 2

A three-layer film, of the following structure, was also used as specimen 2:
Compound A' 10 μm
Compound B' 130 μm
Compound A' 10 μm
The composition of specimen 2 is as follows:
Compound A: 100 parts SEB (molecular weight <120.000 g/mol) 70 parts PP-R Co (PP 23M 10cs264; Rexene)
Compound B: 100 parts SEB (molecular weight <120.000 g/mol) 100 parts PE copolymer (Engage; DOW) (ρ<0.9 g/cm$^3$)
The abbreviations mean:
SEB: Styrene-ethylene-butylene block copolymer
PP-R Co: Polypropylene random copolymer
PP: polyethylene.

Specimen 3

The film according to specimen 3 is a commercially available Nissho film. This is a single-layer film with the following composition:
54% SEB
23-35% PP
5-23% EAA.
The abbreviations mean:
SEB: Styrene-ethylene-butylene block copolymer
PP: Polypropylene homopolymer
EAA: Ethylene-acrylic acid polymer.

Example 1

Deformation During Heat Sterilization

In order to investigate the deformation of films during heat sterilization at a temperature of 121° C., in each case a piece of film measuring 1.33 dm$^2$ was heat-sterilized stress-free for 40 minutes. The results were as follows: Shrinkage in longitudinal direction: specimen 1: 3.2%, specimen 2: 11.1%, specimen 3: 0.4%* shrinkage in transverse direction: specimen 1: 1.6%, specimen 2: 2.1%, specimen 3: 0.4%*(* film according to specimen 3 was already previously ETO-sterilized (ethylene oxide-sterilized) and thus supposedly stress-free.)

Example 2

Sticking During Heat Sterilization

In order to investigate the sticking of the films during heat sterilization, empty bags produced from corresponding films were heat-sterilized at a temperature of 121° C. for 40 minutes. The inner surfaces of the bags showed no measurable sticking or agglutination when using the multilayer film according to specimen 1. In contrast to this, when using the multilayer film according to specimen 2, the inner surfaces of the bags were stuck together, and a hydrostatic pressure of approx. 320 mm WS (water column) was necessary to separate them within approx. 90 seconds over a length of 10 cm. When using specimen 3, after heat sterilization the inner surfaces of the bags were clearly stuck together and could not be completely separated even after being subjected for ten minutes to water pressure at 300 mm Hg.

Example 3

Embrittlement Temperature

The embrittlement temperature of the films was investigated in accordance with DIN 53443 T 2. Specimen 1 showed an incipient brittle fracture at −60° C., specimen 2 at −65° C. and specimen 3 at −60° C.

Example 4

Load-Change Resistance

The load-change resistance was determined by tests using a pneumatically-driven test apparatus. The multilayer film was fixed between two halves of a housing. The film lay flat against the bottom of the housing, while a 25-ml spherical cap extended across the top of the housing.

By alternating exposure to a pressure of 1.5 bar the multilayer film was made to oscillate between the spherical cap and the flat surface. The theoretical extension given a uniform deformation of the film was up to 43%. The investigations were carried out at 37° C. with heat-sterilized films corresponding to specimen 1 and specimen 2.

The load-change tests were followed by investigations using light microscopy, REM and air leakage against water, which revealed no tears or holes in the specimens of the multilayer film could be found even after more than 20,000 load changes. Some of the specimens displayed merely a small degree of creasing, which can be attributed to a slight permanent extension in these areas.

Example 5

Gas Permeability

The following table 1 shows the gas permeability of specimens 1, 2 and 3 for $O_2$ and $CO_2$, wherein the $O_2$ gas permeability was determined according to ASTM D-3985, DIN 53380.

TABLE 1

| | Gas permeability | |
|---|---|---|
| Specimen | $O_2$ cm$^3$/m$^2$*d*bar 95% r.H −23° C. | $CO_2$ cm$^3$/m$^2$*d*bar 95% r.H −23° C. |
| 1 | 3425 | 9901 |
| 2 | 3021 | 9628 |
| 3 | 1654 | 4047 |

It can be seen from example 5 that the gas permeability of the film according to the invention according to specimen 1 lies, both for $O_2$ and also for $CO_2$, clearly in particular above that of the commercially available film according to specimen 3.

Example 2 also shows that the multilayer film according to the invention according to specimen 1 displays no measurable tendency to stick during heat sterilization, which is attributable to the fact that the outside layers consist of at least 55% heat-sterilizable styrene-ethylene-propylene block copolymer with an average molecular weight ≥120 000 g/mol and less than 45% polypropylene.

Example 6

A tensile test was carried out with a specimen of the multilayer film of the disposable bag according to the invention. Specimens with a width of 15 mm and a thickness of 120 μm were tested. The test was carried out with specimens which were die-cut both across the extrusion direction (CD) and along the extrusion direction (MD). The structure of the multilayer film was as follows:
  PP/SEBS 8 μm (40% RD 204 CF; Borealis; 60% Septon 8004, Kuraray)
  PE/SEBS 97 μm (25% Tuftec H1062, Asahi; 40% Engage 8003, Dow; 35% Septon 8004, Kuraray)
  PP/SEBS 15 μm (40% RD 204 CF, Borealis; 60% Septon 8004, Kuraray).

The results are shown in the following table 2:

TABLE 2

| Results of the tensile test | | |
|---|---|---|
| | MPa | |
| Modulus of elasticit MD | >50 N/15 mm Tensile strength MD | >500% Tensile extension MD |
| 58 | 62.4 | 579.4 |
| 21 | 62.7 | 628 |

The tensile test was carried out according to DIN EN 527 1-3 at a rate of feed of 1 mm/min.

Comparative test were carried out with films known from the state of the art.

Specimens with a width of 15 mm and a thickness of 200 μm (comparison film 1) and 120 μm (comparison film 2) were likewise tested. The structure of the comparison films was as follows:

Comparison film 1:

| Structure | approx. 200 μm thick |
|---|---|
| Outside approx. 15 μm | 100% polypropylene-ethylene copolymer |
| Middle approx. 160 μm | 35% SEBS, 65% polypropylene-ethylene copolymer |

-continued

| | |
|---|---|
| Inside approx. 20 μm | 80% polypropylene-ethylene copolymer, 20% SEBS |

Comparison film 2:

| | |
|---|---|
| Structure | approx. 180 μm thickness |
| Outside approx. 20 μm | 100% polypropylene-ethylene copolymer |
| Middle approx. 120 μm | 60% SEBS, 40% polypropylene-ethylene copolymer |
| Inside approx. 20 μm | 100% polypropylene-ethylene copolymer |

The results are shown in the following tables 3 (comparison film 1) and 4 (comparison film 2):

TABLE 3

Comparison film 1

| | MPa | | | | | MPa | | | | | |
|---|---|---|---|---|---|---|---|---|---|---|---|
| Modulus of elasticity MD | >12N/15 mm Yield stress MD | >65N/15 mm Tensile strength MD | >8% Stretch extension MD | >550% Tensile extension MD | Modulus of elasticity CD | >10N/15 mm Yield stress CD | >55N/15 mm Tensile strength CD | >8% Stretch extension CD | >500% Tensile extension CD | >20N/15 mm Welding seam | 3-8N/15 mm Peal seam |
| 254 | 30.1 | 114.7 | 10.9 | 631 | 180 | 23.9 | 112.6 | 13.4 | 640 | 44.3 | 4.9 |

TABLE 4

Comparison film 2

| | MPa | | | MPa | | |
|---|---|---|---|---|---|---|
| Modulus of elasticity MD | >55N/15 mm tensile strength MD | >500% tensile extension MD | Modulus of elasticity CD | >55N/15 mm tensile strength CD | >500% tensile extension CD | >20N/15 mm Welding seam |
| 86.9 | 79.8 | 665.9 | 80.7 | 78.3 | 661.5 | 28.5 |

The invention claimed is:

1. A disposable bag comprising a multilayer film for accommodating a fluid, wherein said multilayer film has a tensile elongation in longitudinal direction of 250% to 850%, and in transverse direction of 300% to 1050% and comprises:
   a) a type (A) layer, comprising several components, wherein one component is a styrene-isoprene block copolymer, styrene-ethylene-butylene block copolymer, styrene-ethylene-propylene block copolymer or a mixture thereof, and a further component is polyethylene or a copolymer which comprises ethylene units
   and wherein the proportion of the one component in the type (A) layer lies in the range of 35 wt. % to 99.99 wt. %, relative to the total composition of the type (A) layer and
   b) two or more type (B) layer(s) comprising several components independently of one another, wherein one component is a styrene-ethylene-butylene block copolymer, styrene-ethylene-propylene block copolymer, styrene-isoprene block copolymer or a mixture thereof, and a further component is a polypropylene or a copolymer which comprises propylene units and wherein the proportion of the one component in the type (B) layer lies in the range of 55 wt. % to 99.99 wt. % and the proportion of the further component in the type (B) layer is in the range of 1 wt. % to 45 wt. %, relative to the total composition of the type (B) layer and wherein the type (A) layer is a middle layer having a thickness of ≥100 μm and is surrounded by two type (B) layers having a thickness of ≤40 μm.

2. A disposable bag according to claim 1, wherein the multilayer film has a tear strength in longitudinal direction 300 N/mm² to 350 N/mm² and in transverse direction 220 N/mm² to 270 N/mm².

3. A disposable bag according to claim 1, wherein the multilayer film has a transverse strain ratio μ in the rubber-elastic state of 0.45 to 0.55.

4. A disposable bag according to claim 1, wherein the multilayer film can be extended by up to 500% by a force of 45 N/15 mm to 60 N/15 mm.

5. A disposable bag according to claim 1, wherein the ratio of the external surface of the disposable bag when filled to the maximum to the external surface when unfilled is ≥2/1.

6. A disposable bag according to claim 1, wherein the holding capacity of the disposable bag when filled to the maximum to the holding capacity in the state in which the multilayer film is present unextended is ≥3/1.

7. A disposable bag according to claim 1, wherein the holding capacity of the disposable bag when filled to the maximum lies in the range of 30 L to 120 L.

8. A disposable bag according to claim 1 which contains several chambers.

9. A disposable bag according to claim 8, wherein the chambers are arranged alongside one another in longitudinal direction of the disposable bag.

10. A disposable bag according to claim 8, wherein at least one chamber has a feed line and a drainage line is attached to a different chamber.

11. A disposable bag according to claim 1, wherein the multilayer film comprises a type (A) layer, which contains several components, wherein one of the components is a styrene-ethylene-butylene block copolymer.

12. A disposable bag according to claim 1, wherein the proportion of the further component in the type (A) layer lies in the range of 0.01 wt. % to 65 wt. %, relative to the total composition of the type (A) layer.

13. A disposable bag according to claim 1, wherein the multilayer film comprises one or more type (B) layer(s) which contains several components independently of one another, wherein one of the components is a styrene-ethylene-butylene block copolymer.

14. A disposable bag according to claim 13, wherein the first component in the type (B) layer has an average molecular weight of ≥120000 g/mol.

15. A method of carrying out a medical treatment comprising using a disposable bag of claim 1 or a support apparatus comprising such a bag.

16. A method according to claim 15, for carrying out haemodialysis or peritoneal dialysis.

17. A process for the production of a disposable bag according to claim 1, comprising the following steps:
   a) producing said multilayer film; and
   b) welding said multilayer film into a disposable bag.

18. A disposable bag according to claim 1, wherein the proportion of the one component in said type (A) layer lies in the range of 55 wt. % to 99.99 wt. %.

19. A disposable bag according to claim 1, wherein the proportion of the one component in said type (A) and said type (B) layer lies in the range of 60 wt. % to 99.99 wt. %.

20. A disposable bag according to claim 1, wherein layer (A) has a thickness of ≥300 μm.

* * * * *